United States Patent [19]

Sherwood et al.

[11] Patent Number: 5,282,853
[45] Date of Patent: Feb. 1, 1994

[54] INTRAOCULAR LENS WITH RESILIENT HAPTICS

[75] Inventors: Charles H. Sherwood, Upland; Shiao H. Chang, Arcadia, both of Calif.

[73] Assignee: Iolab Corporation, Claremont, Calif.

[21] Appl. No.: 953,406

[22] Filed: Sep. 29, 1992

[51] Int. Cl.$^5$ .............................................. A61F 2/16
[52] U.S. Cl. ........................................................ 623/6
[58] Field of Search ................................... 623/6, 901

[56] References Cited

U.S. PATENT DOCUMENTS

| | | | |
|---|---|---|---|
| 4,588,406 | 5/1986 | Fedorov et al. | 623/6 |
| 4,676,791 | 6/1987 | Le Master et al. | 623/6 |
| 4,743,255 | 5/1988 | Bardenstein | 623/6 |
| 4,774,036 | 9/1988 | Le Master et al. | 623/6 |
| 4,813,956 | 3/1989 | Gupta | 623/6 |
| 5,037,435 | 8/1991 | Chang et al. | 623/6 |
| 5,089,180 | 2/1992 | Dunks et al. | 623/6 X |

*Primary Examiner*—David Isabella
*Assistant Examiner*—Mary Beth O. Jones
*Attorney, Agent, or Firm*—Joel R. Petrow

[57] ABSTRACT

An improved intraocular lens is disclosed with at least one filamentary haptic composed of a continuous matrix material interspersed with a toughening amount of discrete particles of a multistage, sequentially produced elastomeric polymer. An improved process for preparing a single-piece intraocular lens is also disclosed. The process involves preparing a composite lens blank by molding pellets composed of a continuous polymeric material interspersed with particles of a multistage, sequentially produced elastomeric polymer about a central optic lens core so as to produce a single lens blank having a toughened annular region surrounding the central optic region, and then machining at least one filamentary haptic from the toughened annular region to prepare the lens.

12 Claims, 4 Drawing Sheets

INTRAOCULAR LENS WITH RESILIENT HAPTICS

BACKGROUND OF THE INVENTION

This invention relates to an improved intraocular lens for implantation in the eye following removal of the natural lens during cataract surgery. More specifically, it relates to such an intraocular lens with at least one filamentary support member, or "haptic", which exhibits an increased resistance to breakage during manipulation.

The filamentary haptic of an intraocular lens is designed to facilitate insertion of the lens into the eye and to provide stable fixation of the implanted lens to prevent the lens from decentering. The filamentary haptic is attached to and extends outwardly from the periphery of the optical lens body. Most intraocular lenses have two haptics displayed at positions 180° apart from each other on the optical lens body.

It is critical that the haptic of the lens exhibits adequate resiliency and significant resistance to breakage during use. Although certain haptic materials such as polypropylene offer acceptable resistance to breakage, other conventionally used haptic materials such as polymethylmethacrylate (PMMA) are brittle and are frequently prone to breakage. This problem becomes especially acute when the haptics are lathe cut from a single lens blank to prepare a one-piece lens with integrally attached haptics. The problem of haptic breakage is a serious one, and efforts have been made to provide the haptics with an increased resistance to breakage.

One such effort is disclosed in U.S. Pat. No. 5,037,435. The '435 patent describes preparing intraocular lenses with haptics exhibiting high fracture toughness. The haptics are composed of a polymer matrix with from 0.1 to 0.5 percent by weight of dispersed, solid particles of an inorganic, biocompatible material. The inorganic materials disclosed include titanium dioxide, fumed silica, barium sulfate and copper phthalocyanate. Organic, elastomeric materials such as polybutadiene are also described. Unfortunately, the haptics of these intraocular lenses fail to exhibit significantly increased fracture toughness because the particle concentration in the matrix is too low to have any beneficial impact, and the inorganic materials disclosed do not impart desired toughness properties regardless of concentration. In addition, the incompatibility of conventional elastomeric materials, such as polybutadiene, with a rigid polymer matrix such as PMMA, prevents increasing the concentration of conventional elastomeric particles to an amount necessary to improve breakage resistance without diminishing the physical and mechanical properties of the rigid polymer matrix.

In view of the deficiencies of the prior art, it would be desirable to fabricate an improved intraocular lens with filamentary support haptics that exhibit an enhanced ability to withstand breakage during routine handling.

SUMMARY OF THE INVENTION

The invention is an improved intraocular lens of the type having a central lens body and at least one filamentary haptic attached to and extending outwardly from the periphery of the lens body. The improvement to the intraocular lens relates to the filamentary haptic, which for this invention is composed of a continuous matrix material interspersed with a toughening amount of discrete particles of a multistage, sequentially-produced elastomeric polymer.

In another aspect, the invention is an improved process for making a one-piece intraocular lens. A one-piece intraocular lens is made using this process by machining a single lens blank to form a central lens body and at least one filamentary haptic integrally attached to and extending outwardly from the periphery of the lens body. The improvement in the process relates to first making a lens blank by molding pellets of the appropriate composition about a cylindrical optic lens core. The pellets are composed of a continuous polymer matrix interspersed with a toughening amount of discrete particles of a multistage, sequentially-produced elastomeric polymer. This molding operation results in an integral lens blank having a toughened annular region surrounding a central optic region. The lens blank can then be machined to form at least one filamentary haptic from the toughened annular region in which the filamentary haptic is integrally attached to and extends outwardly from the periphery of a central lens body.

A filamentary haptic of the improved intraocular lens of this invention exhibits surprisingly dramatic resistance to breakage under adverse handling conditions. The process for making this improved lens is surprisingly straightforward and requires only conventional processing equipment. The resistance to breakage is achieved without the loss of the physical or mechanical integrity of the haptic, or any other property which is necessary for proper functioning and use of the haptic. In addition, the properties of the optic lens body remain unchanged.

DETAILED DESCRIPTION OF THE INVENTION

The multistage, sequentially-produced elastomeric polymer particles are critical for imparting the fracture resistance to the matrix material of the filamentary haptic. Processes for preparing such elastomeric polymers are well known, and described, for example, in U.S. Pat. No. 3,793,402, incorporated by reference herein. The overall bulk properties of the polymer particles are such that the elastomeric stages of the particles have a glass transition temperature (Tg) below room temperature and exhibit a sufficiently high molecular weight or are adequately crosslinked to achieve solid, rubber-like properties. An additional important factor in the bulk properties of the particles is that the particles must be compatible or made to be compatible with the matrix material from which the haptic is composed. Unlike conventional elastomeric particles, this compatibility can be achieved when the particles are made using the multistage stage, sequential process.

Figure 1:
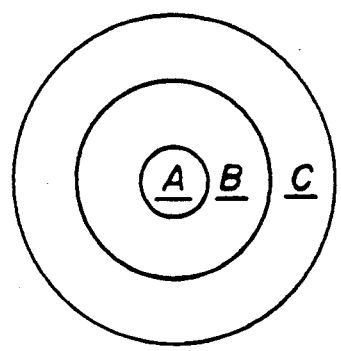
FIG. 1 is a schematic diagram of an individual particle of the multistage, sequentially-produced elastomeric polymer which is dispersed throughout the matrix material of the filamentary haptic of an intraocular lens of this invention.

FIG. 1 illustrates an elastomeric polymer particle used for imparting breakage resistance to the haptic matrix material. As can be seen from FIG. 1, the multistage, sequential production of the polymer yields a polymer particle that has three substantially discrete layers of polymeric materials exhibiting different properties.

The inner "core" layer, denoted in FIG. 1 as Component A, is made in the first stage of the production of the sequentially-produced elastomeric polymer. It should be nonelastomeric and glassy. It must have a Tg greater than room temperature, preferably 60° C. or greater, and can be composed of a polymer of an ester of acrylic or methacrylic acid, which polymer is crosslinked to provide its desired properties. The preferred polymer in the core layer is crosslinked PMMA.

Surrounding the core component of the polymer particle is a sequentially-produced intermediate layer, Component B, and a separate and distinct outer layer, or "shell", Component C. Component B is an elastomeric polymer, preferably composed of a polymer of an alkyl acrylate, such as butyl acrylate. Alternatively, it can be composed of butadiene or substituted butadiene (substituted with, for example, isoprene, chloroprene and 2,3 dimethylbutadiene). The elastomers of this stage are those that have a Tg of 25° C. or less. Preferred are those elastomers having a Tg less than 10° C., and most preferred are those elastomers having a Tg less than −10° C. Component B imparts the bulk elastomeric properties to the polymeric particles. Component C is a relatively hard polymer similar to the polymer of the core component of the particle. As used herein, a "hard" polymer refers to a glassy polymer which has a Tg above room temperature, preferrably 50° C. or higher. The material from which Component C is made is preferably crosslinked PMMA, but critically, it must be made up of a material which is compatible with the matrix material from which the haptic is composed. For purposes of this invention, the material from which Component C is made is "compatible" with the haptic matrix material if Component C has a chemical composition similar to the composition of the haptic matrix.

The finely divided, discrete elastomeric polymer particles should be of a particle size in the submicron range. If the particles are substantially larger than submicron size, then the particles may have a tendency to agglomerate and therefore create nonuniformity in the properties of the filamentary haptic. Advantageously, the particle size ranges from about 100 to about 300 nanometers (nm), preferably from about 160 to about 280 nm.

The continuous matrix material from which the haptic is made is preferably polymeric. The most preferred matrix material is composed of crosslinked PMMA, although other materials such as copolymers of methyl methacrylate and other biocompatible polymers can be used.

The amount of polymer particles necessary to provide significant toughening to the filamentary haptic can generally range from about 5 to about 65 percent of the weight of the haptic, preferably from about 35 to about 45 percent. This relatively high solids loading is possible because of the compatibility of the multi-stage, sequentially-produced particles with the polymer matrix. If the amount of particles is less than 5 percent, then the likelihood of achieving a beneficial effect on the impact resistance of the haptic is small. If the amount of toughening particles is greater than about 65 percent, then there is a strong possibility that the overall physical and mechanical properties of the haptic may be compromised.

The most preferred formulation for the preparation of the filamentary haptic is commercially available in the form of molding pellets (often referred to as "molding powder"), which consists of individual pellets that are composed of the matrix material interspersed with a toughening amount of the discrete particles of the multistage, sequentially-produced elastomeric polymer. A particularly preferred molding powder resin from which the haptics can be made is Plexiglas ® DR ® acrylic molding pellets.

Figure 2:
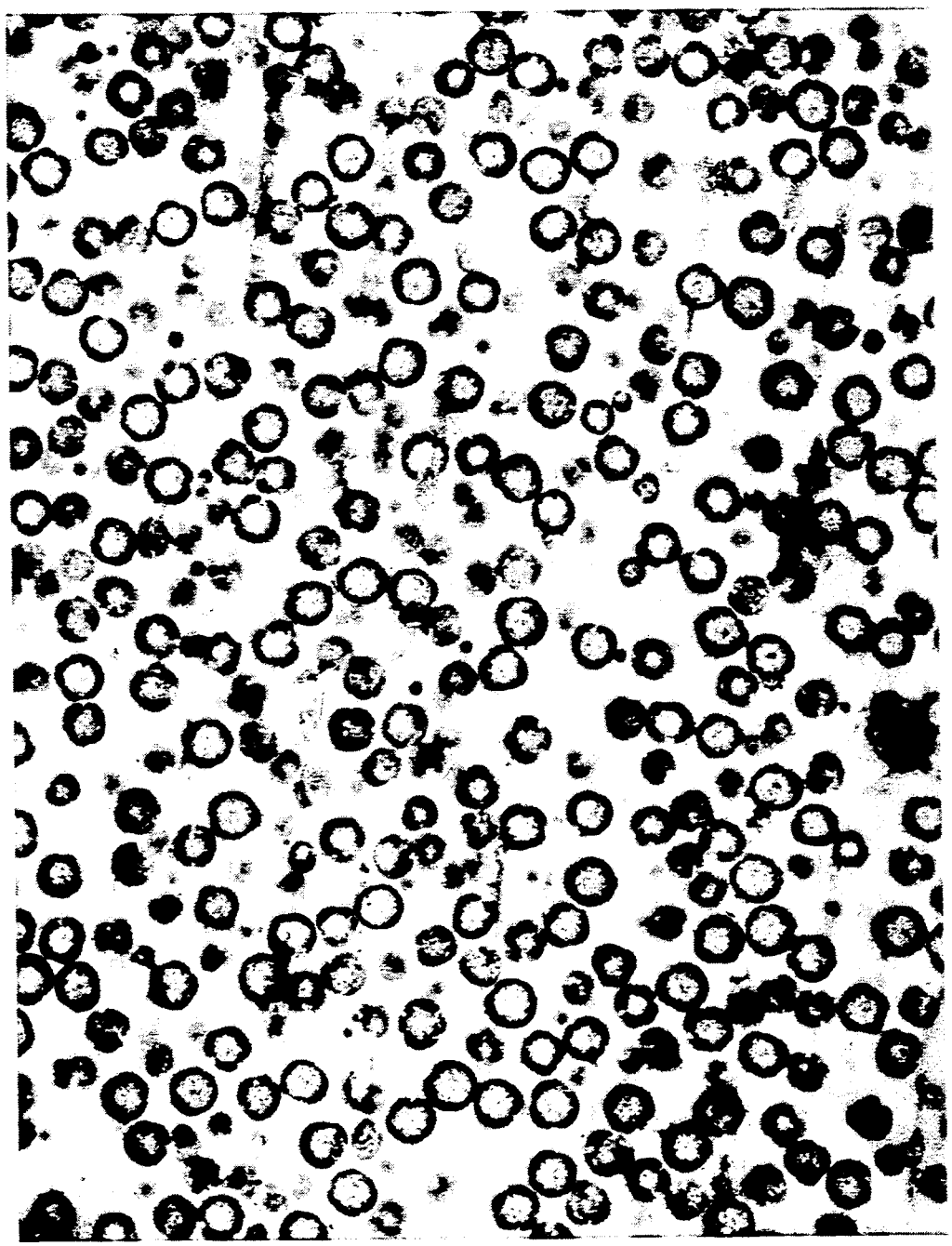
FIG. 2 is photomicrograph illustration at a magnification of 25,000× showing the morphology of the filamentary haptic.

FIG. 2 represents a photomicrograph of a toughened filamentary haptic of the improved intraocular lens of this invention. The photomicrograph clearly depicts discrete elastomeric particles, which in this case have been made using the multistage process, interspersed within a continuous matrix. The outer shell layer of each of the discrete particles is well defined by the dark ring surrounding the periphery of each of the particles. The shell layer prevents the discrete particles from agqlomerating even at relatively high concentrations, so that uniformly improved haptic performance can be achieved.

The filamentary haptic can be attached to the optic lens body of the intraocular lens through chemical, thermal or other known physical processes. Preferably, two haptics are attached to the periphery of the optic lens body at diametrically opposed positions on the optic.

Chemically, the toughened haptics can be attached to the optic lens body by a copolymerization process. This process involves placing an optic core in a suitable tubular mold, pouring into the mold a polymerizable composition suitable for preparing the matrix material of the haptic, which composition contains the toughening particles, and then polymerizing the curable resin in the mold to prepare an optic lens blank having a toughened annular region from which the haptic members can be lathe cut. Ideally, the annular region configured about the optic core is colored by adding a suitable dye into the matrix material before polymerization. See, for example, U.S. Pat. Nos. 5,089,180 and 4,961,746.

Alternatively, the filamentary haptics can be attached to the optic lens body by conventional physical means, for example, by staking. Bonding can also be achieved by conventional solvent welding processes.

The preferred process for attaching the filamentary haptic to the lens body of the intraocular lens is a process in which the haptics are integrally attached to the lens body in a one-piece intraocular lens configuration. This processing can be most readily achieved either by compression molding or injection molding. In fact, the desired haptic composition lends itself perfectly to such processing because of the availability of molding powder in the form of pellets which are composed of the toughened elastomeric polymer particles interspersed in the desired polymeric matrix of the haptic.

In the compression molding process, the optic core, or optical lens body, is placed in a suitable mold configured to allow for the molding of the annular haptic region about the central optic core. Once the optic core is placed in the mold, the molding powder pellets of the desired composition, for example, Plexiglas ® DR ® acrylic molding pellets, are placed in the mold completely surrounding the optic core. The mold is then heated to a temperature sufficient to soften the pellets, and then pressure is applied by compression in the mold to bring the optic core and the softened pellets into contact for proper fusion and shaping of the composite lens blank. Compression also induces necessary degassing of pockets of air which form between individual pellets during the fusing process. Following compression at an adequate pressure for a suitable period of time, the mold is released and the temperature of the prepared composite blank is lowered. The composite blank can then be machined on a lathe to fabricate the filamentary haptics from the toughened annular region surrounding the optic core of the lens blank.

Another method for preparing a composite lens blank from which the haptics can be machined for the preparation of an improved one-piece intraocular lens of this invention would be the use of conventional injection molding processes well known in the art. Similar to the process scheme for compression molding, the injection molding process would utilize molding pellets composed of the desired matrix material of the haptics toughened with appropriate multistage, sequentially produced polymeric particles. In one embodiment, the pellets can be injection molded to form the configuration of an annular ring, or "donut", which can then be placed over an optical core rod which would form the lens body of the intraocular lens. By application of heat and pressure, the toughened donut could be fused to the optic rod for the preparation of the lens blank similar in configuration to the lens blank made by the compression molding process described above.

As used herein, the term "pellets" is used expansively to refer to not only traditional pellets but also derivatives of pellets which can be formed using conventional processing techniques. For example, molding pellets can be milled or pulverized to make a fine, powder-like substance. For the purposes of this invention, such a substance or any colorable imitation thereof would still be considered "pellets".

Other means for integrally attaching the filamentary haptic to the lens body of the one-piece intraocular lens are well within the scope of those skilled in this art. For example, in addition to the methods illustrated above for such attachment, the molding powder formulation for the preparation of the haptics can be extruded about an optic core rod through a conventional wire extrusion dye used for the preparation of coated wires and coated tubular members.

In another embodiment of this invention, the haptics are tinted or colored to provide a better visual aid during surgery by incorporation of a suitable dye into the haptic composition. Although many means for accomplishing the incorporation of a dye into the haptic composition described herein can be envisioned, one such method would involve compounding the dye into the desired molding pellet formation for the haptic composition by conventional extrusion techniques. Similarly, the dye can be incorporated into the proper molding composition in a compression or injection mold.

The following examples are designed to illustrate the preferred embodiments of this invention, and should not be construed in any way to limit the full breadth and scope of that which is defined as the invention in the appended claims.

BRITTLENESS TEST METHOD

Figure 3:
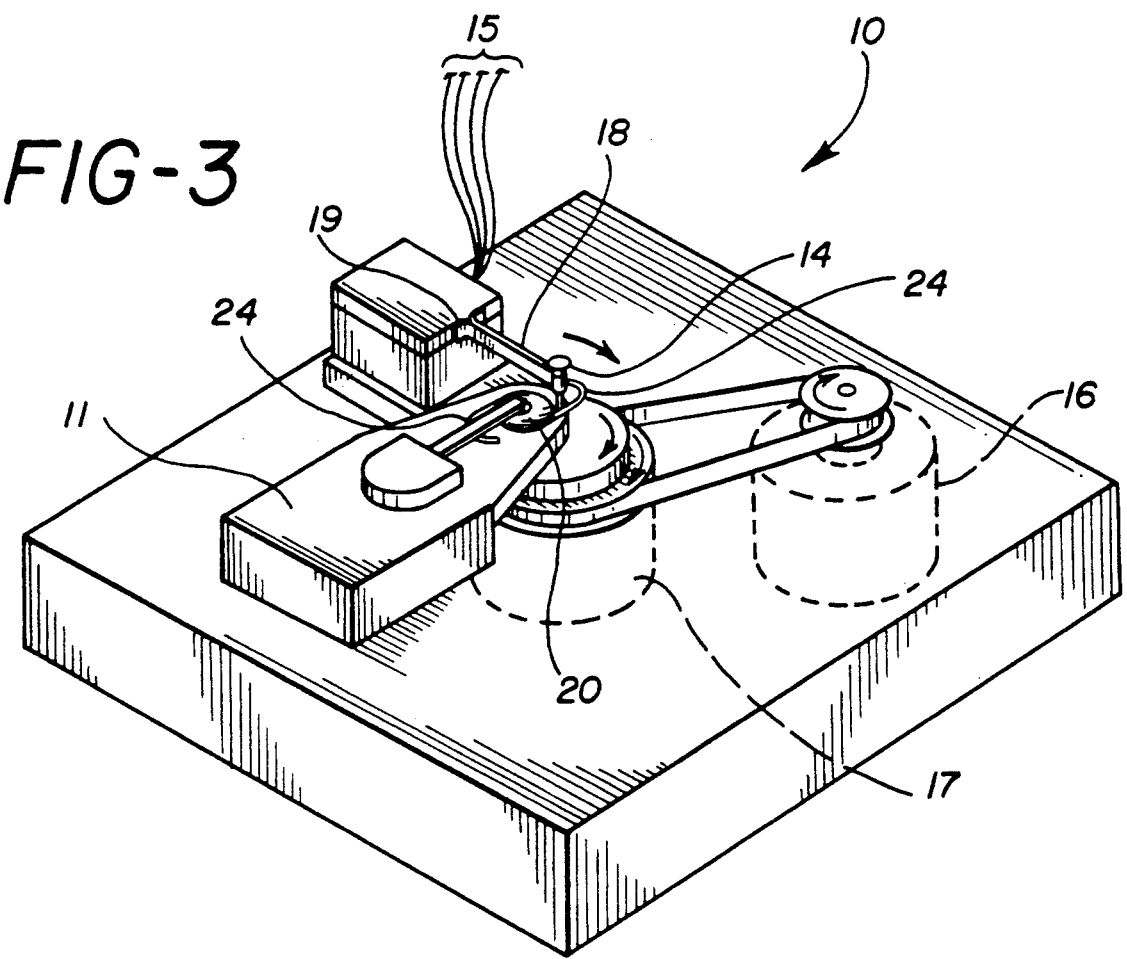
FIG. 3 is a perspective view of a brittleness tester used for determining the resistance to breakage of the haptic of an intraocular lens.
Figure 4:
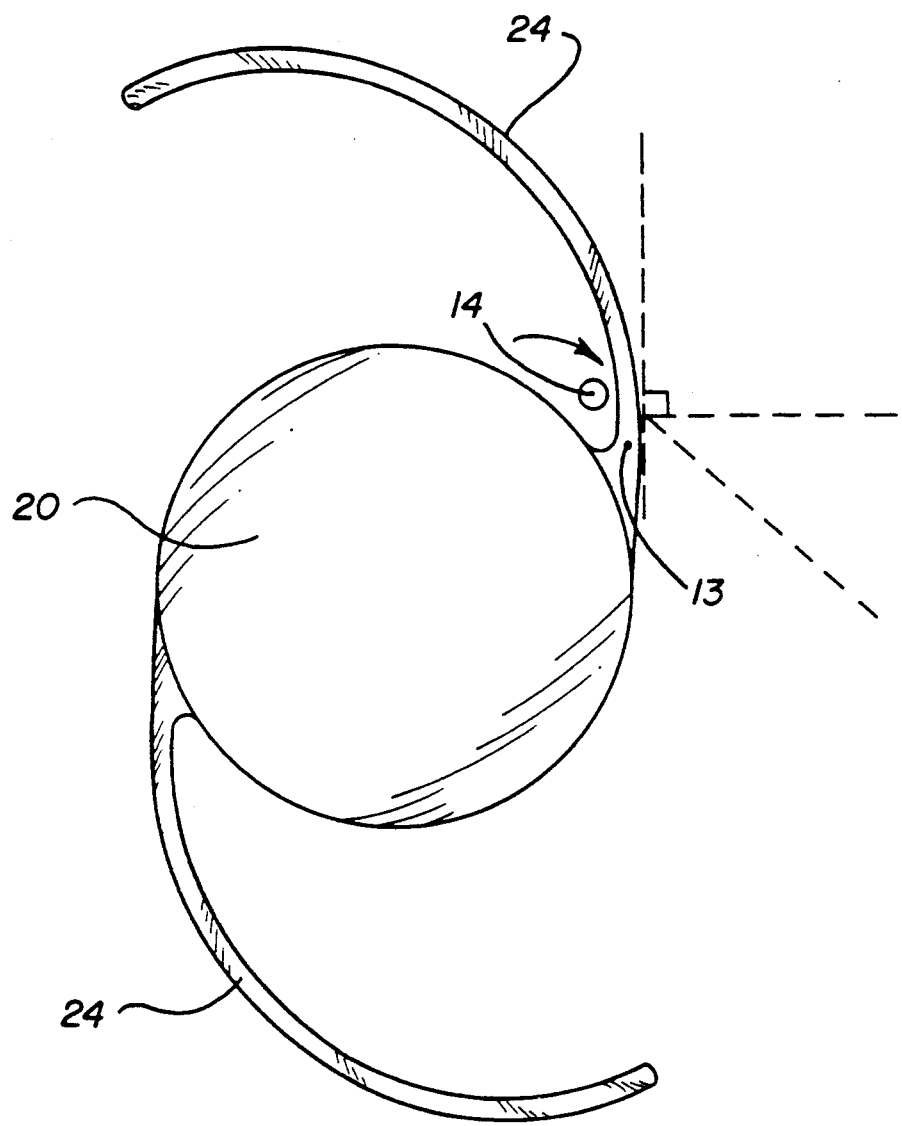
FIG. 4 is a top plan view of a one piece intraocular lens showing the location and direction of rotation used in brittleness testing.

FIG. 3 shows a brittleness tester 10 used for determining the resistance to breakage of the haptic of an intraocular lens. The lens 20 is placed in a fixture 1 that holds the lens securely by the lens body of the lens. As shown more clearly in FIG. 4, the optic-haptic junction of the lens is placed at the center of rotation 13 on the tester. The tester operates by moving the rotatable pin 14 against one of the haptics 24. This forces the haptic to rotate around the center of rotation 13 in a clockwise direction. The speed of rotation can be controlled from a computer interface 15, and can be varied up to 900 degrees per second using stepper motor 16. The maximum rotation angle is 140°. The encoder 17 accurately measures the rotation angle and feeds the information through the computer interface. The rotating arm 18 and strain gauge 19 allow the accurate measurement of force necessary to move the haptic. The individual haptic thickness and width measurements are entered into a computer in order to calculate stress from the force measurements. A stress-angle curve obtained through brittleness testing is similar to a typical stress strain curve obtained by conventional mechanical testing. Stress strain testing gives an indication of the strength of a material and also its toughness. Toughness is defined as the area under the stress-strain curve or stress-angle curve. The brittleness test is, therefore, an effective tool to evaluate haptic performance against breakage.

EXAMPLE 1-Compression Molded Lens

Figure 5:
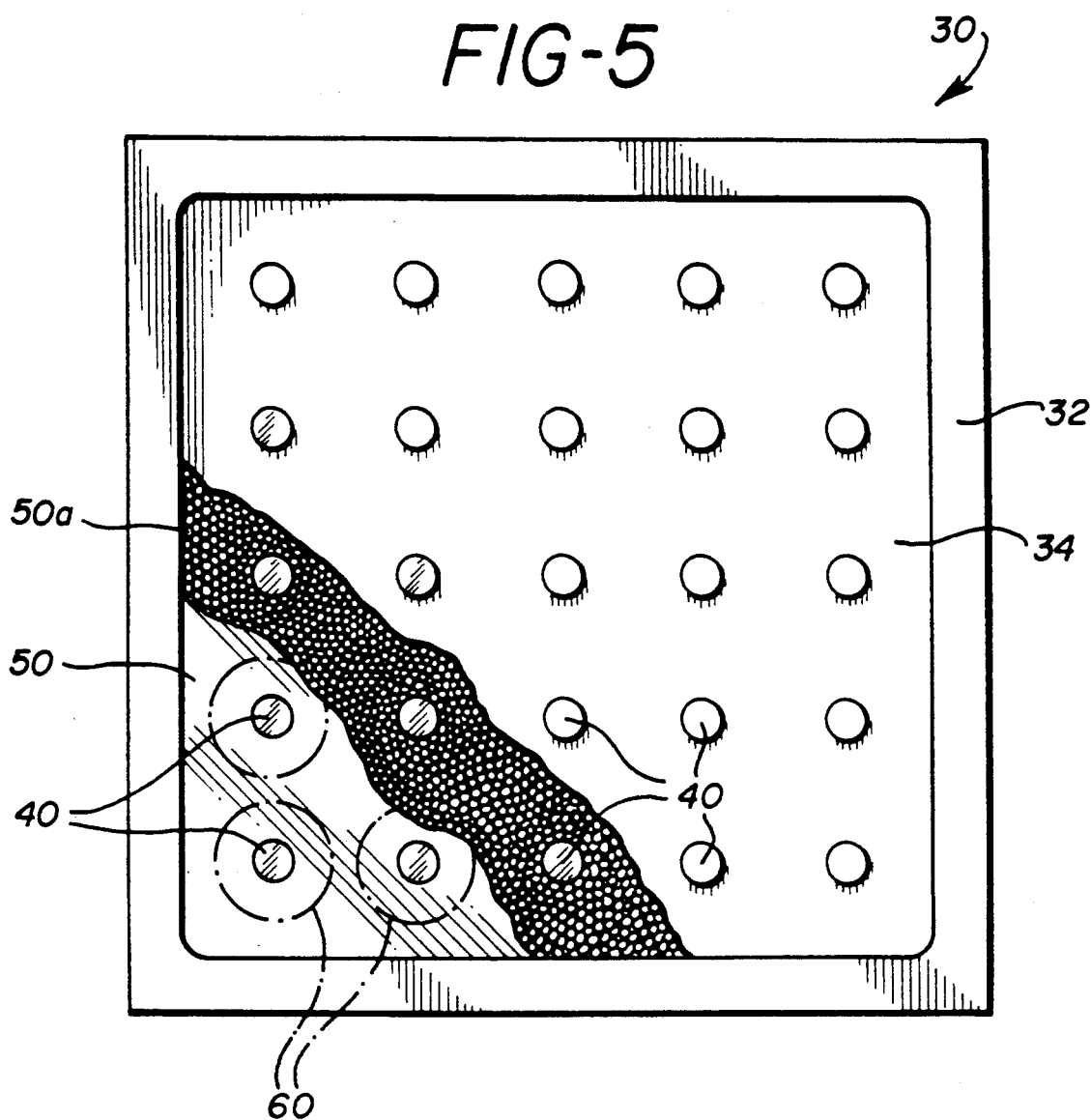
FIG. 5 is a top plan view of a mold chase used to mold the toughened resin around optic cores.
Figure 6:
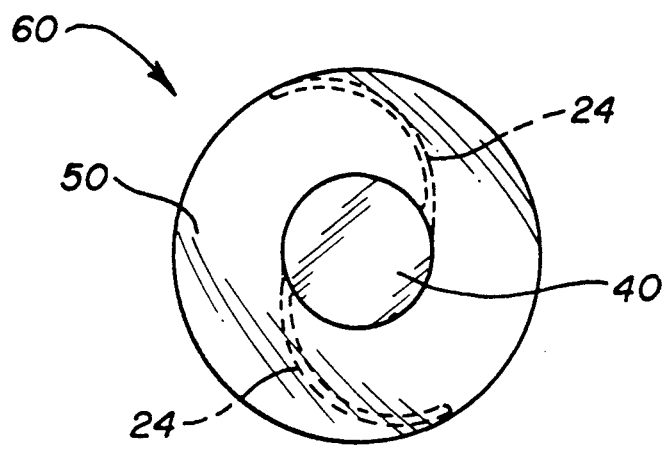
FIG. 6 is a top plan view of a composite blank containing toughened PMMA resin around an optic core.

Referring now to FIGS. 5 and 6 in combination, an intraocular lens with toughened, impact-modified haptics is fabricated from a composite rod blank 60 containing an annular region 50 of molded Plexiglas ® DR ® acrylic resin centered about, and bonded to, a PMMA optic core rod 40. A number of composite rod blanks can be produced simultaneously by compression molding of the DR ® resin around the optic core rods in a mold chase 30. The mold chase has a mold plate 32 containing a plurality of cavities for the optic core rods, and an open area 34. DR ® pellets 50a are loaded in the open area surrounding the optic core rods. The mold chase is then heated at 210±5° C. for 10 minutes in a press prior to molding at a pressure of 10,000 lbs. The composite blanks, each about 16 mm in diameter, are then machined from the molded sheet. The lens is then fabricated from the molded composite blank using standard lens manufacturing processes. The brittleness test results of the impact modified haptics and a competitive lens, Control #1, are presented in Table 1.

The lenses tested as Control #1 are made from a proprietary material formulated with a low concentration of biocompatible particulates in the haptics to supposedly give increased haptic toughness.

TABLE 1

| | Brittleness Test Results | | | |
|---|---|---|---|---|
| Ex. No. | Sample ID | Model | Max. Angle or Angle at Break deg | Fracture Rate |
| Control #1 | Intraocular Lens | ORC Flexeon ® C410 | 37 | 100 |
| #1 | Intraocular Lens | Plexiglas ®DR ® acrylic resin | >140 | 0 |

TABLE 1 -continued

Brittleness Test Results

| Ex. No. | Sample ID | Model | Max. Angle or Angle at Break deg | Fracture Rate |
|---------|-----------|-------|----------------------------------|---------------|
|         |           | toughened haptics |                        |               |

As shown from the data in Table 1, lenses from Control #1 do not show improved resistance to haptic fracture. In contrast, the data indicate no haptic breakage upon brittleness testing for the lens of this invention having the toughened haptic material. Thus, the results demonstrate the ductile and flexible nature of the haptics toughened with the DR ® acrylic resin.

EXAMPLE 2-Injection Molded Lens

An intraocular lens with impact modified colored haptics is fabricated from a composite blank containing an annular region of molded Plexiglas ® DR ® acrylic resin and colored dye centered about, and molded to, a PMMA optic core. In this example, D&C Violet #2 dye is pre-mixed in the Plexiglas ® DR ® resin at 0.15% w/w. The composite blanks are produced by injection molding of the pre-mixed violet DR ® resin around the optic rod in a mold. The mold consists of a single cavity Round Mate style tool with a pocket to insert the optic rod. The optic rod is preheated to 220° C. before placing in the mold. The molding conditions used are listed below.

| | |
|---|---|
| Resin temperature: | 260° C. |
| Mold temperature: | 105° C. |
| Injection pressure: | 23,000 psi |
| Injection speed: | 6.86 in³/sec |

The lens is then fabricated from the injection molded composite blank using standard lens manufacturing processes. The brittleness test results for this lens, as well as a competitive lens denominated as Control #1 and a conventional lens denominated as Control #2, are presented in Table 2.

TABLE 2

Brittleness Test Results

| Ex. No. | Sample ID | Model | Max. Angle or Angle at Break deg | Fracture Rate |
|---------|-----------|-------|----------------------------------|---------------|
| Control #1 | Intraocular Lens | ORC Flexeon ® C410 | 37 | 100 |
| Control #2 | Intraocular Lens | Iolab UV grade PMMA 8590B | 56 | 100 |
| #2 | Intraocular Lens | Violet Plexiglas ® DR ® acrylic resin toughened haptics | >140 | 5 |

As can be seen from the data in Table 2, lenses made from Control #2, which do not have toughened haptics, show typical haptic fracture characteristics for untoughened PMMA lenses. The lenses tested as Control #1 are made from a proprietary material formulated with a low concentration of biocompatible particulates in the haptics to supposedly give increased toughness. Lenses from Control #1 do not show improved resistance to haptic fracture as compared to the untoughened PMMA lenses. In contrast, the lenses of this invention made with haptics toughened with the DR ® resin show a dramatically reduced fracture rate in comparison to those of the controls.

We claim:

1. An improved intraocular lens having a central lens body and at least one filamentary haptic attached to and extending outwardly from the periphery of said lens body, the improvement wherein the filamentary haptic is composed of a continuous matrix material interspersed with a toughening amount of discrete particles of a multistage, sequentially-produced elastomeric polymer, wherein each of said discrete particles has an inner core layer of a glassy polymer, an intermediate layer of an elastomeric polymer, and an outer shell layer of a glassy polymer which is compatible with said continuous matrix material.

2. The intraocular lens of claim 1 wherein the core layer is composed of a polymer of cross-linked acrylic or methacrylic acid.

3. The intraocular lens of claim 2 wherein the core layer is composed of crosslinked PMMA.

4. The intraocular lens of claim 3 wherein the intermediate layer is composed of a polymer from the group consisting of an alkyl acrylate, a substituted butadiene and an unsubstituted butadiene.

5. The intraocular lens of claim 3 wherein the intermediate layer is composed of a polymer of butyl acrylate.

6. The intraocular lens of claim 5 wherein the outer shell layer is composed of crosslinked PMMA.

7. The intraocular lens of claim 6 wherein the size of each of the discrete particles ranges from about 100 to about 300 nm.

8. The intraocular lens of claim 6 wherein the size of each of the discrete particles ranges from about 160 to about 280 nm.

9. The intraocular lens of claim 8 wherein the continuous matrix material is polymeric.

10. The intraocular lens of claim 9 wherein the polymeric matrix is crosslinked PMMA.

11. The intraocular lens of claim 10 wherein the toughening amount of discrete particles interspersed in the matrix material is between about 5 to about 65 percent of the weight of the haptic.

12. The intraocular lens of claim 10 wherein the toughening amount of discrete particles interspersed in the matrix material is between about 35 to about 45 percent of the weight of the haptic.

* * * * *